(12) United States Patent
Katsu et al.

(10) Patent No.: US 12,052,817 B2
(45) Date of Patent: Jul. 30, 2024

(54) ELASTIC WIRING BOARD

(71) Applicant: Murata Manufacturing Co., Ltd., Nagaokakyo (JP)

(72) Inventors: Hayato Katsu, Nagaokakyo (JP); Keisuke Nishida, Nagaokakyo (JP); Kentaro Usui, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 242 days.

(21) Appl. No.: 17/652,207

(22) Filed: Feb. 23, 2022

(65) Prior Publication Data

US 2022/0183151 A1 Jun. 9, 2022

Related U.S. Application Data

(63) Continuation of application No. PCT/JP2021/017998, filed on May 12, 2021.

(30) Foreign Application Priority Data

May 21, 2020 (JP) ................................ 2020-088921

(51) Int. Cl.
*H05K 1/02* (2006.01)
*H05K 1/03* (2006.01)
*H05K 1/11* (2006.01)

(52) U.S. Cl.
CPC ......... *H05K 1/0283* (2013.01); *H05K 1/0393* (2013.01); *H05K 1/118* (2013.01); *H05K 2201/0133* (2013.01)

(58) Field of Classification Search
CPC ........................... H05K 1/0259; H05K 1/0283
See application file for complete search history.

(56) References Cited

U.S. PATENT DOCUMENTS

| 6,316,734 | B1 * | 11/2001 | Yang | .................... | H05K 1/0259 |
| | | | | | 428/209 |
| 2016/0374615 | A1 | 12/2016 | Tsukada et al. | | |
| 2018/0303418 | A1 | 10/2018 | Rogers et al. | | |
| 2020/0102417 | A1 | 4/2020 | Hatakeyama et al. | | |
| 2021/0059046 | A1 | 2/2021 | Koshimizu | | |

FOREIGN PATENT DOCUMENTS

| JP | H02172733 A | 7/1990 |
| JP | 2003224349 A | 8/2003 |
| JP | 2017152687 A | 8/2017 |
| JP | 2018114302 A | 7/2018 |
| JP | 2019165048 A | 9/2019 |
| JP | 2019165408 A | 9/2019 |
| JP | 2019220247 A | 12/2019 |
| JP | 2020055300 A | 4/2020 |

OTHER PUBLICATIONS

International Search Report issued for PCT/JP2021/017998, date of mailing Aug. 3, 2021.
Japanese Office Action issued for Japanese Patent Application No. 2021-576148, date of Japanese Office Action Mar. 22, 2021.

* cited by examiner

*Primary Examiner* — Jeremy C Norris
(74) *Attorney, Agent, or Firm* — ArentFox Schiff LLP

(57) ABSTRACT

An elastic wiring board that includes an elastic substrate; a plurality of electrode wirings having elasticity; and an ion-migration resistant layer between at least a first electrode wiring of the plurality of electrode wirings and the elastic substrate.

20 Claims, 1 Drawing Sheet

ELASTIC WIRING BOARD

CROSS REFERENCE TO RELATED APPLICATIONS

The present application is a continuation of International application No. PCT/JP2021/017998, filed May 12, 2021, which claims priority to Japanese Patent Application No. 2020-088921, filed May 21, 2020, the entire contents of each of which are incorporated herein by reference.

FIELD OF THE INVENTION

The present invention relates to an elastic wiring board.

BACKGROUND OF THE INVENTION

In recent years, the state of the human body has been managed by acquiring and analyzing biological information.

As a method of acquiring and managing biological information, there is known a method of attaching, to a living body, an elastic wiring board composed of an elastic substrate and electrode wiring arranged on the elastic board.

For example, Patent Document 1 has disclosed an elastic wiring board including a plurality of elastic wiring substrates and at least one of a plurality of elastic wiring portions provided on each of the main surfaces facing the plurality of elastic substrates. The elastic wiring portions provided on each of the main surfaces are conductive to each other via connection parts interposed therebetween.

In addition, Patent Document 1 has disclosed that as a method of reducing the occurrence of ion migration, an interlayer elastic substrate is arranged between main surfaces facing the elastic substrates, and the moisture permeability of the interlayer elastic substrate is lowered less than that of the elastic substrate, thereby allowing suppression of the occurrence of ion migration.

Patent Document 1: Japanese Patent Application Laid-Open No. 2017-152687

SUMMARY OF THE INVENTION

However, although the moisture permeability of the interlayer elastic substrate is adjusted to be lower than that of the elastic substrate as in the elastic wiring board disclosed in Patent Document 1, the elastic substrate that has absorbed moisture may still cause occurrence of ion migration.

The present invention has been made to solve the above problem, and an object of the present invention is to provide an elastic wiring board having excellent ion migration resistance.

The elastic wiring board of the present invention comprises an elastic substrate; a plurality of electrode wirings having elasticity; and an ion-migration resistant layer between at least a first electrode wiring of the plurality of electrode wirings and the elastic substrate.

The present invention can provide an elastic wiring board having excellent ion migration resistance.

DETAILED DESCRIPTION OF THE INVENTION

Hereinafter, the elastic wiring board of the present invention will be described.

However, the present invention is not limited to the following configuration, and can be appropriately modified and applied without changing the gist of the present invention. A combination of two or more of the individual desirable configurations described below is also the present invention.

The elastic wiring board of the present invention comprises an elastic substrate; a plurality of electrode wirings having elasticity; and an ion-migration resistant layer between at least a first electrode wiring of the plurality of electrode wirings and the elastic substrate.

In the elastic wiring board of the present invention, the ion-migration resistant layer is an insulating layer having low moisture absorption or a moisture repellent layer.

The elastic substrate that has absorbed moisture in a high humidity environment is considered to reduce insulation resistance, easily diffuse metal ions, and thus cause occurrence of ion migration.

The insulating layer having low moisture absorption hardly diffuses metal ions, regardless of whether the elastic substrate has absorbed moisture. Therefore, when the insulating layer having low moisture absorption is provided between at least a part of the electrode wiring and the elastic substrate, the diffusion of metal ions is blocked between the electrode wirings to suppress ion migration.

Whereas, the moisture repellent layer has a property of blocking the movement of water with the moisture repellent layer interposed therebetween. Therefore, regardless of whether the elastic substrate has absorbed moisture, the diffusion of metal ions hardly occurs. Therefore, when the moisture repellent layer is provided between at least a part of the electrode wiring and the elastic substrate, the diffusion of metal ions is blocked between the electrode wirings to suppress ion migration.

Figure 1:
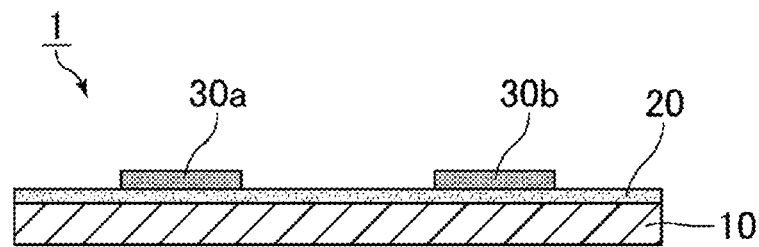
FIG. 1 is a cross-sectional view schematically showing an example of the elastic wiring board of the present invention.

FIG. 1 is a cross-sectional view schematically showing an example of the elastic wiring board of the present invention.

As shown in FIG. 1, an elastic wiring board 1 is composed of an elastic substrate 10, electrode wirings 30a and 30b, and an insulating layer having low moisture absorption 20 provided between the electrode wirings 30a and 30b and the elastic substrate 10. The electrode wiring 30a and the electrode wiring 30b have different potentials from each other.

When the elastic wiring board 1 is used, a voltage is applied between the electrode wiring 30a and the electrode wiring 30b. As a result, an electric field is generated between the electrode wiring 30a and the electrode wiring 30b at a position with the elastic substrate 10 interposed therebetween. When there is no insulating layer having low moisture absorption 20, the electrode wiring 30a, the electrode wiring 30b, and the elastic substrate 10 are in contact with each other, and the elastic substrate 10 is in a state of absorbing moisture, diffusion of metal ions progresses inside the elastic substrate 10 and thus ion migration occurs.

In contrast, in the elastic wiring board 1, the insulating layer having low moisture absorption 20 is provided between the electrode wiring 30a and the elastic substrate 10 and between the electrode wiring 30b and the elastic substrate 10, respectively. The insulating layer having low moisture absorption 20 hardly diffuses metal ions constituting the electrode wiring. Therefore, in the elastic wiring board 1, the occurrence of ion migration can be suppressed.

An elastic with board with a moisture repellent layer provided instead of an insulating layer having low moisture absorption is also a configuration of the elastic wiring board of the present invention. The moisture repellent layer has a property of blocking the movement of moisture when interposed between the electrode wirings and the elastic substrate, and therefore diffusion of metal ions hardly occurs in the moisture repellent layer regardless of whether the elastic substrate absorbs moisture. Therefore, the occurrence of ion migration can be suppressed.

As described above, the insulating layer having low moisture absorption and the moisture repellent layer can suppress the occurrence of ion migration. Therefore, in the present description, the insulating layer having low moisture absorption and the moisture repellent layer are collectively referred to as an ion-migration resistant layer.

The elastic wiring board of the present invention may include both the insulating layer having low moisture absorption and the moisture repellent layer.

The elastic substrate preferably includes a urethane resin or an acrylic resin.

Examples of the urethane resin include thermoplastic polyurethane.

Examples of the acrylic resin include an elastomer composed of an acrylic copolymer resin.

When the elastic wiring board is attached to a living body, the thickness of the elastic substrate is preferably 1000 μm or less, more preferably 100 μm or less, from the viewpoint of not inhibiting the expansion and contraction of the surface of the living body. In addition, the thickness of the elastic substrate is preferably 10 μm or more.

Examples of the method for producing the elastic substrate include a method of molding a urethane resin or an acrylic resin into a predetermined shape (for example, a sheet shape) by, for example, injection molding, pressure molding, and tape casting method.

The electrode wiring is preferably composed of a mixture of conductive particles and an elastomer. Examples of such a mixture include a mixture of a metal powder such as silver, copper, and nickel as conductive particles and an elastomer resin such as an epoxy resin, a urethane resin, an acrylic resin, and a silicone resin. The elastomer resin may be used in combination of two or more.

From the viewpoint of reducing the resistance of the electrode wiring, the conductive particles are preferably silver particles. When the conductive particles are silver particles, ion migration particularly occurs. The elastic wiring board of the present invention has excellent ion migration resistance, and therefore ion migration hardly occurs although silver is used as a material constituting the conductive particles.

The average particle size D50 of the conductive particles is preferably 0.01 μm to 10 μm.

The average particle size D50 of the conductive particles can be measured by a laser diffraction/scattering method.

The shape of the conductive particles is not limited to a spherical shape, and may be a flat shape or a shape having protrusions.

The thickness of the electrode wiring is preferably 100 μm or less, more preferably 50 μm or less. In addition, the thickness of the electrode wiring is preferably 1 μm or more.

The electrode wiring can be formed, for example, by a method in which a dispersion or slurry with a mixture of conductive particles and an elastomer dispersed in a solvent is printed on the surface of an elastic substrate or an ion-migration resistant layer and then dried.

In the elastic wiring board of the present invention, the plurality of electrode wirings may be provided at the same position in the thickness direction of the elastic wiring board, or may be provided at different positions.

An example of providing a plurality of electrode wirings at different positions in the thickness direction of the elastic wiring board includes a case where the electrode wirings are arranged on both sides of the elastic substrate.

In the elastic wiring board of the present invention, three or more electrode wirings may be arranged.

When three or more electrode wirings are arranged, two or more electrode wirings having the same potential may be arranged as long as two or more of potentials exist as the potentials of the electrode wirings.

The insulating layer having low moisture absorption refers to an insulating layer having a moisture absorption ratio of 2.0% or less measured in accordance with ASTM standard D570.

The moisture absorption ratio of the insulating layer having low moisture absorption is preferably 1.5% or less, more preferably 1.0% or less.

The insulating layer having low moisture absorption preferably includes a resin having low moisture absorption such as silicone resin, acrylic resin, olefin resin, modified urethane resin, vinyl chloride resin, polyester, polyamide, polyolefin, polyethylene, and polypropylene, or a paraxylylene-based polymer.

An insulating layer having low moisture absorption including an insulating resin having low moisture absorption can be obtained by, for example, a method of preparing a dispersion with the insulating resin having low moisture absorption dispersed in a solvent, applying the dispersion by, for example, printing on an elastic substrate, and drying; or a method of applying a monomer dispersion including a monomer to be an insulating resin having low moisture absorption by polymerization onto an elastic substrate by, for example, printing, and then polymerizing the monomer by means such as heat or UV exposure.

The insulating layer having low moisture absorption, including a paraxylylene-based polymer, can be obtained by depositing the paraxylylene-based polymer on an elastic substrate.

Examples of the method of printing the dispersion on the elastic substrate include screen printing, gravure printing, and inkjet printing.

The thickness of the insulating layer having low moisture absorption obtained by applying and drying the dispersion is preferably 1 μm to 100 μm, and more preferably 10 μm to 30 μm.

When the thickness of the insulating layer having low moisture absorption obtained by applying and drying the dispersion is 1 μm to 100 μm, appropriate hardness can be imparted to the elastic wiring board.

The thickness of the insulating layer having low moisture absorption obtained by vapor deposition is preferably 0.1 μm to 10 μm, and more preferably 1 μm to 10 μm.

When the thickness of the insulating layer having low moisture absorption obtained by vapor deposition is more than 10 μm, the ion migration resistance is hardly improved. Therefore, from the viewpoint of production cost, the thickness of the insulating layer having low moisture absorption obtained by vapor deposition is preferably 10 μm or less.

The moisture repellent layer is a layer having a contact angle to water of 90° or more.

The contact angle of the moisture repellent layer to water is preferably 100° or more, and more preferably 120° or more.

Examples of the method of forming the moisture repellent layer include a method of applying a commercially available moisture repellent agent onto an elastic substrate by, for example, printing and then treating with heat as necessary. Examples of the commercially available moisture repellent agent include F-based (fluorine-based) moisture repellent agents and Si-based (silicone-based) moisture repellent agents.

In the elastic wiring board of the present invention, the ion-migration resistant layer may be provided on the entire surface of the elastic substrate, or may be provided only on a part thereof. For example, in an elastic wiring board 1 shown in FIG. 1, the insulating layer having low moisture absorption 20 is provided on the entire surface of the elastic substrate 10; however, the insulating layer having low moisture absorption 20 may be provided only between the electrode wiring 30a and the elastic substrate 10, and/or only between the electrode wiring 30b and the elastic substrate 10, that is, only in the portion where the electrode wiring and the elastic substrate face each other.

Figure 2:
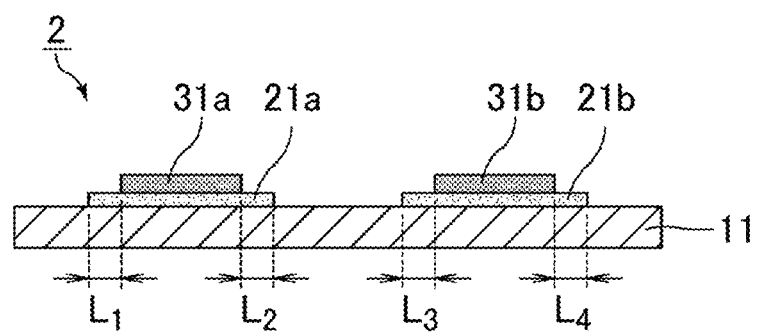
FIG. 2 is a cross-sectional view schematically showing another example of the elastic wiring board of the present invention.

FIG. 2 is a cross-sectional view schematically showing another example of the elastic wiring board of the present invention.

The elastic wiring board 2 shown in FIG. 2 is composed of an elastic substrate 11, an electrode wirings 31a and 31b, an insulating layer having low moisture absorption 21a arranged between the electrode wiring 31a and the elastic substrate 11, and an insulating layer having low moisture absorption 21b arranged between the wiring 31b and the elastic substrate 11. The electrode wirings 31a and 31b are provided on the insulating layers having low moisture absorption 21a and 21b, respectively, and are not in direct contact with the elastic substrate 11. In addition, the insulating layer having low moisture absorption 21 is not provided on the elastic wiring board 2, and there is a portion where the elastic substrate 11 is exposed.

In the elastic wiring board 2, the external dimensions of the insulating layers having low moisture absorption 21a and 21b are larger than the external dimensions of the electrode wirings 31a and 32b, respectively. When the external shape of the insulating layer having low moisture absorption 21a and the external shape of the electrode wiring 31a are overlapped in a plan view, the shortest distance from the end of the external shape of the electrode wiring 31a to the end of the external shape of the insulating layer having low moisture absorption 21a (the length indicated by the double-headed arrows $L_1$ and $L_2$ in FIG. 2) is preferably 20 μm or more, and more preferably 100 μm or more. Setting the distance $L_1$ and the distance $L_2$ to 20 μm or more can improve the insulation between the electrode wiring and the elastic substrate. The distance $L_1$ and the distance $L_2$ are preferably 3000 μm or less. Setting the distance $L_1$ and the distance $L_2$ to 3000 μm or less can minimize the irritation caused by the ion-migration resistant layer to a living body and thus the biocompatibility can be improved.

When the external shape of the insulating layer having low moisture absorption 21b and the external shape of the electrode wiring 31b are overlapped in a plan view, the shortest distance from the end of the external shape of the electrode wiring 31b to the end of the external shape of the insulating layer having low moisture absorption 21b (the length indicated by the double-headed arrows $L_3$ and $L_4$ in FIG. 2) is preferably 20 μm or more, and more preferably 100 μm or more. In addition, the distance $L_3$ and the distance $L_4$ are preferably 3000 μm or less.

The ion-migration resistant layer is preferably provided between two electrode wirings having different potentials and an elastic substrate.

Two electrode wirings having different potentials have a relatively high potential (high potential electrode) for one wiring and a relatively low potential (ground electrode) for the other wiring. In this case, the position where the ion-migration resistant layer is arranged may be a position in contact with the high potential electrode, a position in contact with the ground electrode, or a position in not contact with any one of the high potential electrode and the ground electrode. However, from the viewpoint of preventing the diffusion of metal ions, the ion-migration resistant layer is preferably provided at a position in contact with the high potential electrode that is the starting point of diffusion.

The elastic wiring board 2 shown in FIG. 2 is an example in which an ion-migration resistant layer is provided at both the position in contact with the high potential electrode and the position in contact with the ground electrode. Therefore, the wiring board obtained by removing any one of the insulating layer having low moisture absorption 21a and the insulating layer having low moisture absorption 21b from the elastic wiring board 2 shown in FIG. 2, and directly providing the electrode wiring 31a or 31b on the elastic substrate 11 is also the elastic wiring board of the present invention.

The diffusion of metal ions from the electrode wiring to the elastic substrate occurs when the elastic substrate is arranged between the electrode wirings having different potentials. Therefore, the diffusion of metal ions does not occur in the elastic substrate arranged between the electrode wirings having the same potential, and thus it is not necessary to provide the ion-migration resistant layer.

Figure 3:
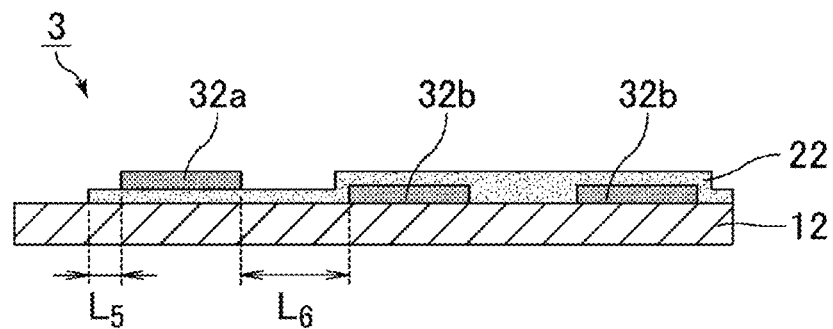
FIG. 3 is a cross-sectional view schematically showing still another example of the elastic wiring board of the present invention.

FIG. 3 is a cross-sectional view schematically showing still another example of the elastic wiring board of the present invention.

The elastic wiring board 3 shown in FIG. 3 is composed of an elastic substrate 12, electrode wirings 32a and 32b, and an insulating layer having low moisture absorption 22 arranged between the electrode wiring 32a and the elastic substrate 12. The electrode wiring 32a is provided on the insulating layer having low moisture absorption 22 and is not in direct contact with the elastic substrate 12. Whereas, the two electrode wirings 32b are in direct contact with the elastic substrate 12.

The electrode wiring 32a and the electrode wiring 32b have different potentials from each other; however, the two electrode wirings 32b have the same potential. Therefore, the insulating layer having low moisture absorption 22 is provided between the electrode wirings 32a and the electrode wirings 32b having different potentials; however, the insulating layer having low moisture absorption 22 is not provided between the electrode wirings 32b having the same potential.

In addition, the insulating layer having low moisture absorption 22 is not provided on the elastic wiring board 3, and there is a portion where the elastic substrate 12 is exposed.

When determining whether or not the ion-migration resistant layer is provided between the electrode wirings, the shortest distance between the electrode wirings in the plan view or the cross-sectional view is not used as a reference; however, the diffusion route of metal ions between the electrode wirings when a voltage is applied is used as a reference.

In addition, in the elastic wiring board 3, the external dimensions of the insulating layer having low moisture absorption 22 are larger than the external dimensions of the electrode wiring 32a. When the external shape of the insulating layer having low moisture absorption 21 and the external shape of the electrode wiring 30a are overlapped in a plan view, the shortest distance from the end of the external shape of the electrode wiring 32a to the end of the external shape of the insulating layer having low moisture absorption 22 (the length indicated by the double-headed arrows $L_5$ in FIG. 3) is preferably 20 µm or more, and more preferably 100 µm or more.

Setting the distance $L_5$ to 20 µm or more can improve the insulation between the electrode wiring and the elastic substrate.

The distance $L_5$ is preferably 3000 µm or less. Setting the distance $L_5$ to 3000 µm or less can minimize the irritation caused by the ion-migration resistant layer to a living body and thus the biocompatibility can be improved.

The external shape of the ion-migration resistant layer arranged between the electrode wiring and the elastic substrate preferably has a larger area than the external shape of the electrode wiring and is similar to the external shape of the electrode wiring. When the external shape of the ion-migration resistant layer and the external shape of the electrode wiring are overlapped, the external shape of the ion-migration resistant layer is preferably such that the external shape of the electrode wiring protrudes outward by 20 µm or more and 3000 µm or less. The protrusion amount (length) is a length corresponding to the distance $L_1$, the distance $L_2$, the distance $L_3$, and the distance $L_4$ described in FIG. 2, and the distance $L_5$ described in FIG. 3.

The plan view shape of the ion-migration resistant layer may be a shape that covers two or more electrode wirings.

At least one of the electrode wirings having different potentials is preferably provided directly above the ion-migration resistant layer.

When one electrode wiring is arranged directly above the ion-migration resistant layer and the other electrode wiring is arranged directly under the same ion-migration resistant layer, the shortest distance between one electrode arranged directly above the ion-migration resistant layer and the other electrode wiring arranged directly under the ion-migration resistant layer (the length indicated by the double arrow $L_6$ in FIG. 3) is preferably 20 µm or more, and more preferably 100 µm or more.

When the distance from one electrode wiring to the other electrode wiring is more than 3000 µm in a plan view, it is preferable to provide a region in which the ion-migration resistant layer is not provided between the two electrode wirings.

In the elastic wiring board 3 shown in FIG. 3, the electrode wiring 32a and the electrode wiring 32b having different potentials are separated by the same insulating layer having low moisture absorption 22, and when the insulating layer having low moisture absorption is provided only directly under the electrode wiring 32a, the amount of protrusion of the ion-migration resistant layer from the electrode wiring 31a when the ion-migration resistant layer and the electrode wiring 31a are viewed in a plan view is preferably 20 µm or more, and preferably 100 µm at any position. The upper limit of the amount of protrusion is preferably 3000 µm or less.

The elastic wiring board of the present invention may include, for example, an electrode or an electronic component as a configuration other than the electrode wiring and the ion-migration resistant layer.

The electrode serves to receive biological signals when the elastic wiring board is attached to a living body.

The electrode is preferably a gel electrode. Using the gel electrode can easily attach the elastic wiring board to a living body. The gel electrode is composed of a conductive gel material including, for example, water, alcohol, a moisturizer, and an electrolyte. Examples of such gel materials include hydrogels.

However, the electrode including conductive particles shall be treated as electrode wiring.

Examples of electronic components include capacitors, inductors, diodes, resistors, and amplifiers.

EXAMPLES

Hereinafter, examples of the elastic wiring board of the present invention disclosed more specifically will be described. The present invention is not limited to these examples.

Example 1

A 40 µm-thick thermoplastic polyurethane resin sheet was cut into 150 mm×150 mm to provide an elastic substrate. A dispersion with a modified silicone resin dispersed in a solvent was applied onto the elastic substrate and dried to be formed into an insulating layer having low moisture absorption having a thickness of 10 µm on the elastic substrate. Furthermore, on the insulating layer having low moisture absorption, two electrode wirings having a line width of 0.5 mm and a thickness of 25 µm were formed in parallel at intervals of 1000 µm by using silver paste, and the elastic wiring board according to Example 1 was obtained.

The moisture absorption ratio of the thermoplastic polyurethane resin sheet was 2.2%. In addition, the moisture absorption ratio of the insulating layer having low moisture absorption was 0.11%.

Examples 2 to 4

The elastic wiring boards according to Examples 2 to 4 were obtained in the same manner as in Example 1, except that the composition of the insulating layer having low moisture absorption was changed to that shown in Table 1.

Comparative Example 1

The elastic wiring board according to Comparative Example 1 was obtained in the same manner as in Example 1, except that the insulating layer having low moisture absorption was not provided.

(Reliability Test)

The elastic wiring boards according to Examples 1 to 4 and Comparative Example 1 were left in a state where a DC current of 5V was applied between the two electrode wirings under the conditions of a temperature of 40° C. and a relative humidity of 95%, and the time until a short circuit occurred (short circuit time) was measured. The results are shown in Table 1. ">24 hour" means that a short circuit did not occur after 24 hour leaving period.

TABLE 1

| | Insulating layer having low moisture absorption | | Short circuit time |
|---|---|---|---|
| | Resin | moisture absorption ratio [%] | |
| Example 1 | Modified silicone resin | 0.11 | >24 hour |
| Example 2 | Polystyrene resin | 0.08 | >24 hour |
| Example 3 | Modified polyurethane resin | 1.1 | >24 hour |
| Example 4 | Acrylic resin | 0.5 | >24 hour |
| Comparative Example 1 | — | — | 10 min |

From the results in Table 1, it was confirmed that the elastic wiring board provided with the insulating layer having low moisture absorption obtained by applying and drying the dispersion had excellent ion migration resistance in a high humidity environment.

Examples 5 to 8

The elastic wiring boards according to Examples 5 to 8 were obtained in the same manner as in Example 1, except that the distance L between the electrode wiring and the insulating layer having low moisture absorption was changed as shown in Table 2 by changing the printing pattern of the insulating layer having low moisture absorption, and a reliability test was performed. The elastic substrate and the insulating layer having low moisture absorption constituting the elastic wiring board according to Examples 5 to 8 were the same as those in Example 1. The test conditions for the reliability test were the same as in Examples 1 to 4 and Comparative Example 1. The results are shown in Table 2. The results of Comparative Example 1 are also shown in Table 2.

">12 hour" means that a short circuit did not occur after 12 hour leaving period.

TABLE 2

| | Distance between electrode wiring and insulating layer having low moisture absorption [μm] | Short circuit time |
|---|---|---|
| Example 5 | 10 | >12 hour |
| Example 6 | 20 | >24 hour |
| Example 7 | 100 | >24 hour |
| Example 8 | 300 | >24 hour |
| Comparative Example 1 | — | 10 min |

From the results in Table 2, the distance L between the electrode wiring and the insulating layer having low moisture absorption is preferably 20 μm or more in order to prevent ion migration. In addition, in consideration of production variations, the distance L between the electrode wiring and the insulating layer having low moisture absorption is more preferably 100 μm or more.

Examples 9 to 12

The elastic wiring boards according to Examples 9 to 12 were obtained in the same manner as in Example 1, except that a paraxylylene-based polymer was vapor-deposited to provide an insulating layer having low moisture absorption, instead of applying and drying a dispersion on the elastic substrate, and a reliability test was performed. The test conditions for the reliability test were the same as in Examples 1 to 4 and Comparative Example 1. The results are shown in Table 3. The results of Comparative Example 1 are also shown in Table 3.

In addition, the moisture absorption ratio of the insulating layer having low moisture absorption obtained by vapor-depositing a paraxylylene-based polymer was 0.1% or less.

TABLE 3

| | Insulating layer having low moisture absorption Film thickness [μm] | Short circuit time |
|---|---|---|
| Example 9 | 0.1 | >12 hour |
| Example 10 | 1 | >24 hour |
| Example 11 | 5 | >24 hour |
| Example 12 | 10 | >24 hour |
| Comparative Example 1 | — | 10 min |

From the results in Table 3, it was confirmed that the elastic wiring board provided with the insulating layer having low moisture absorption by vapor deposition had excellent ion migration resistance in a high humidity environment. In addition, it was confirmed that the thickness of the insulating layer having low moisture absorption provided by vapor deposition might be 0.1 μm or more and was preferably 1 μm or more.

Examples 13 and 14

The elastic wiring boards according to Examples 13 and 14 were obtained in the same manner as in Example 1, except that the moisture repellent agent shown in Table 4 was applied onto the surface of the elastic substrate and heat-treated at 80° C. to be formed into a moisture repellent layer, instead of applying and drying a dispersion on the elastic substrate. The contact angle of the moisture repellent layer to water was measured, and a reliability test was performed.

The test conditions for the reliability test were the same as in Examples 1 to 4 and Comparative Example 1. The results are shown in Table 4. The results of Comparative Example 1 are also shown in Table 4. The contact angle of the thermoplastic polyurethane resin sheet to water was 70°.

TABLE 4

| | Moisture repellent layer | | Short circuit time |
|---|---|---|---|
| | Type | Contact angle [°] | |
| Example 13 | F-based moisture repellent agent | 110 | >24 hour |
| Example 14 | Si-based moisture repellent agent | 110 | >24 hour |
| Comparative Example 1 | — | — | 10 min |

From the results in Table 4, it was confirmed that the elastic wiring board provided with the moisture repellent layer had excellent ion migration resistance in a high humidity environment.

DESCRIPTION OF REFERENCE SYMBOLS

1, 2, 3: Elastic wiring board
10, 11, 12: Elastic substrate 20, 21a, 21b, 22: Insulating layer having low moisture absorption
30a, 30b, 31a, 31b, 32a, 32b: Electrode wiring

The invention claimed is:

1. An elastic wiring board, comprising:
an elastic substrate;
a plurality of electrode wirings having elasticity; and
a low moisture absorption insulating layer including a low moisture absorption resin between at least a first electrode wiring of the plurality of electrode wirings and the elastic substrate.

2. The elastic wiring board according to claim 1, wherein the low moisture absorption insulating layer has a moisture absorption ratio of 2.0% or less as measured in accordance with ASTM standard D570.

3. The elastic wiring board according to claim 1, wherein the low moisture absorption insulating layer is a moisture repellant layer, and a contact angle of the moisture repellent layer to water is 100° or more.

4. The elastic wiring board according to claim 1, wherein the elastic substrate includes a urethane resin or an acrylic resin.

5. The elastic wiring board according to claim 1, wherein the first electrode wiring include a mixture of conductive particles and an elastomer.

6. The elastic wiring board according to claim 1, wherein external dimensions of the low moisture absorption insulating layer are larger than external dimensions of the first electrode wiring.

7. The elastic wiring board according to claim 6, wherein an external shape of the low moisture absorption insulating layer and an external shape of the first electrode wiring are overlapped in a plan view of the elastic wiring board, and a shortest distance from an end of the external shape of the first electrode wiring to an end of the external shape of the low moisture absorption insulating layer is 20 μm or more.

8. The elastic wiring board according to claim 7, wherein the shortest distance from the end of the external shape of the first electrode wiring to the end of the external shape of the low moisture absorption insulating layer is 20 μm to 3000 μm.

9. The elastic wiring board according to claim 6, wherein an external shape of the low moisture absorption insulating layer and an external shape of the first electrode wiring are overlapped in a plan view of the elastic wiring board, and a shortest distance from an end of the external shape of the first electrode wiring to an end of the external shape of the low moisture absorption insulating layer is 100 μm or more.

10. The elastic wiring board according to claim 9, wherein the shortest distance from the end of the external shape of the first electrode wiring to the end of the external shape of the low moisture absorption insulating layer is 100 μm to 3000 μm.

11. The elastic wiring board according to claim 1, wherein a thickness of the elastic substrate is 10 μm to 1000 μm.

12. The elastic wiring board according to claim 1, wherein a thickness of the first electrode wiring is 1 μm to 100 μm.

13. The elastic wiring board according to claim 1, wherein a thickness of the low moisture absorption insulating layer is 1 μm to 100 μm.

14. The elastic wiring board according to claim 1, wherein a thickness of the low moisture absorption insulating layer is 10 μm to 30 μm.

15. The elastic wiring board according to claim 1, wherein a thickness of the low moisture absorption insulating layer is 0.1 μm to 10 μm.

16. The elastic wiring board according to claim 1, wherein a second electrode wiring of the plurality electrode wirings is in direct contact with the elastic substrate.

17. The elastic wiring board according to claim 16, wherein the first electrode wiring and the second electrode wiring have different potentials.

18. The elastic wiring board according to claim 16, wherein the low moisture absorption insulating layer covers the second electrode wiring.

19. The elastic wiring board according to claim 16, wherein a shortest distance between the first electrode wiring and the second electrode wiring is 20 μm or more.

20. The elastic wiring board according to claim 16, wherein a shortest distance between the first electrode wiring and the second electrode wiring is 100 μm or more.

* * * * *